(12) United States Patent  
Taylor et al.

(10) Patent No.: US 7,740,483 B2
(45) Date of Patent: Jun. 22, 2010

(54) PORTABLE DEMONSTRATION APPARATUS AND METHOD FOR THE COMPARISON OF LUBRICANTS AND/OR LUBRICANT ADDITIVES

(75) Inventors: William P. Taylor, Mentor, OH (US); Kathleen O. Havelka, Mentor, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 918 days.

(21) Appl. No.: 11/259,590

(22) Filed: Oct. 26, 2005

(65) Prior Publication Data

US 2006/0093491 A1     May 4, 2006

Related U.S. Application Data

(60) Provisional application No. 60/623,469, filed on Oct. 29, 2004.

(51) Int. Cl.
*G09B 25/00* (2006.01)

(52) U.S. Cl. .................. 434/388; 73/10; 73/53.05; 73/54.01; 73/54.12

(58) Field of Classification Search .............. 434/365, 434/388; 74/10, 54.12; 184/48.2, 67
See application file for complete search history.

(56) References Cited

U.S. PATENT DOCUMENTS

| | | | | | |
|---|---|---|---|---|---|
| 1,977,244 | A | * | 10/1934 | Putnam et al. | 434/388 |
| 2,045,897 | A | * | 6/1936 | Clegg | 434/388 |
| 2,175,638 | A | * | 10/1939 | Rau | 434/367 |
| 2,221,731 | A | * | 11/1940 | Biggs | 434/388 |
| 2,700,228 | A | * | 1/1955 | Fainman | 434/388 |
| 2,738,670 | A | * | 3/1956 | Coene | 73/54.33 |
| 3,267,722 | A | * | 8/1966 | Gordon | 73/54.12 |
| 3,766,773 | A | * | 10/1973 | Limpert | 73/54.12 |
| 4,484,468 | A | * | 11/1984 | Gau et al. | 73/54.35 |
| 4,731,028 | A | * | 3/1988 | Dickerson | 434/388 |
| 4,942,759 | A | * | 7/1990 | Beers | 73/54.12 |
| 2002/0116987 | A1 | * | 8/2002 | Braithwaite et al. | 73/54.01 |
| 2003/0147073 | A1 | * | 8/2003 | Abraham et al. | 356/318 |
| 2003/0236855 | A1 | * | 12/2003 | Quesnel, Jr. | 709/217 |

OTHER PUBLICATIONS

Viscocity Introduction : Friction at the Molecular Level, Michael Flowler, UVA Jun. 26, 2007, Source:- http://galileo.phys.virginia.edu/classes/152.mf1i.spring02/Viscosity.pdf; pp. 1, 3-8.*

Friction in Fluids, Princeton University 1996, Source:- http://www.physics.princeton.edu/~mcdonald/examples/ph101_1996/ph101lab8_96.pdf. pp. 1-5.*

* cited by examiner

*Primary Examiner*—Cameron Saadat
*Assistant Examiner*—Bruk A Gebremichael
(74) *Attorney, Agent, or Firm*—Christopher D. Hilker; David M. Shold

(57) ABSTRACT

A portable apparatus and method for demonstrating different characteristics of different fluids that includes different fluid sumps or chambers for receiving samples of the different fluids. A test shaft having different portions that are immersed in the different fluid samples in the chambers is driven by an electric drive motor at a substantially constant speed while substantially the same amount of friction or force is applied to the different portions of the test shaft at different times to increase the resistance presented to the drive motor. The additional amount of current drawn or power absorbed by the motor or strain induced in the motor drive shaft during the application of such friction or force to the different portions of the test shaft is monitored and compared to provide a comparison of the friction or power loss characteristics of the different fluid samples.

16 Claims, 1 Drawing Sheet

PORTABLE DEMONSTRATION APPARATUS AND METHOD FOR THE COMPARISON OF LUBRICANTS AND/OR LUBRICANT ADDITIVES

CROSS-REFERENCE TO RELATED APPLICATIONS

This application claims the benefit of U.S. Provisional Application Ser. No. 60/623,469, filed Oct. 29, 2004.

FIELD OF THE INVENTION

The present invention relates to a portable apparatus and method for demonstrating and comparing certain properties of different fluids including particularly the friction or power loss characteristics of lubricants and lubricant additives including engine lubricant treatments for vehicle motor oils and the like.

BACKGROUND OF THE INVENTION

It is common practice to compare certain characteristics of different fluids including, for example, the friction and power loss characteristics of lubricants and lubricant additives. However, it would be advantageous to be able to immediately demonstrate such a prospective benefit obtained by using one fluid over another for training and exhibition purposes using a portable demonstration apparatus to establish and compare certain characteristics of different fluids and display the comparison data interpersonally, in a small group, organizationally, publicly, and/or through mass media.

SUMMARY OF THE INVENTION

The present invention relates to a portable apparatus and method for establishing and comparing certain characteristics of different fluids to demonstrate a prospective benefit obtained by using one fluid over another.

In accordance with one aspect of the invention, the portable demonstration apparatus includes two fluid sumps or chambers in which certain characteristics of different fluid samples placed in the fluid chambers are established and compared.

In accordance with another aspect of the invention, a control system compares and displays comparative data of certain characteristics of the different fluid samples in the fluid sumps or chambers.

In accordance with another aspect of the invention, the comparison data is obtained at a point of presentation or sale.

In accordance with another aspect of the invention, the comparison data is viewed interpersonally, in a small group, organizationally, publicly, and/or through mass media.

In accordance with another aspect of the invention, the comparison data is obtained through a communications network which may be the Internet.

In accordance with another aspect of the invention, the fluids are lubricants or lubricant additives such as engine lubricant treatments for vehicle motor oils.

In accordance with another aspect of the invention, a test shaft having different portions immersed in the different fluid samples in the chambers may be driven by the drive shaft of an electric drive motor at a substantially constant speed while substantially the same amount of friction or force is applied to the different portions of the test shaft at different times to increase the resistance presented to the drive motor. The additional current drawn or absorbed by the drive motor or additional strain induced in the drive motor shaft to keep the test shaft rotating at a constant speed during the application of such friction or force to the different portions of the test shaft is monitored and compared to provide a comparison of the friction or power loss characteristics of the different fluid samples.

In accordance with another aspect of the invention, the friction or force is applied to the different portions of the test shaft by individually activated friction shoes.

In accordance with another aspect of the invention, the fluid chambers, drive motor and test shaft are contained in a common housing.

In accordance with another aspect of the invention, the portable demonstration apparatus is packaged with its own power supply in a portable hand carrying type case.

These and other advantages, features and aspects of the present invention will become apparent as the following description proceeds.

To the accomplishment of the foregoing and related ends, the invention, then, comprises the features hereinafter more fully described and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

The present invention may be more readily understood by reference to the following drawings in which.

DETAILED DESCRIPTION

The portable demonstration apparatus and method of the present invention provide for the demonstration and comparison of different characteristics of different fluids for training and exhibition purposes and the like. A preferred embodiment of the invention provides for the demonstration and comparison of friction or power loss characteristics of different lubricants and/or lubricant additives including engine lubricant treatments for passenger car or other vehicle motor oils.

Figure 1:
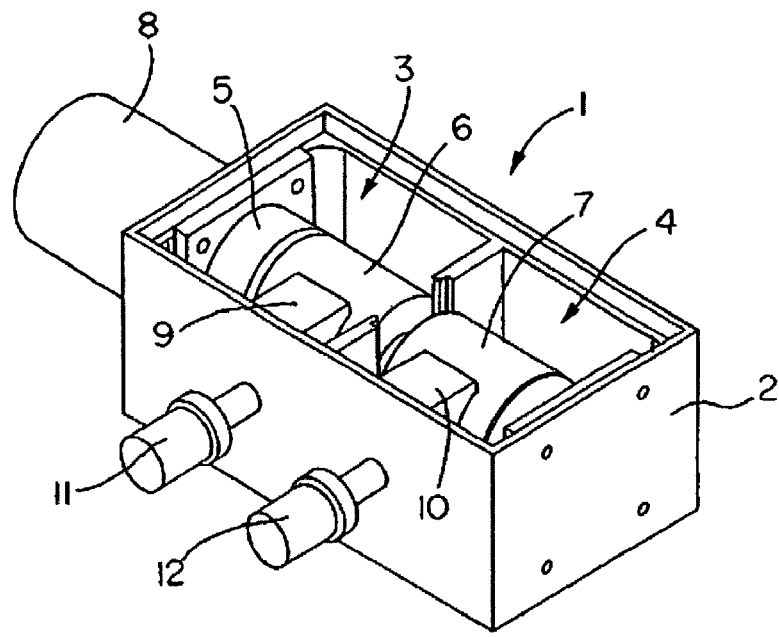
FIG. 1 is a schematic perspective view of one form of portable demonstration apparatus of the present invention.

Referring now in detail to the drawings, wherein the same reference numbers are used to designate like parts, and initially to FIG. 1, there is shown one form of portable demonstration apparatus 1 of the present invention including a housing 2 containing a plurality of individual fluid sumps or chambers 3, 4 for receiving samples of the different fluids to be compared. A test shaft 5 having different portions 6, 7 extending through and into the different fluid chambers 3,4 for immersion in the fluid samples contained therein is suitably coupled at one end to the drive shaft of an electric drive motor 8 for rotating the test shaft at a substantially constant speed.

Separate friction members or shoes 9, 10 located within the different fluid chambers 3, 4 are selectively movable into and out of frictional engagement with the respective portions 6, 7 of the test shaft 5 as by actuation of respective pistons 11, 12 operatively connected to the friction members. These friction members 9, 10 may be activated at different times to apply substantially the same friction or force to the different portions 6, 7 of the test shaft while immersed in the different fluid samples and rotated at a substantially constant speed by the drive motor 8. This increases the resistance presented to the drive motor which causes the drive motor to draw more current and absorb more power and induces more strain in the drive shaft to rotate the test shaft at a constant speed. The increased drive shaft strain may be measured by a strain element including but not limited to a resistive strain gage affixed to the drive shaft coupling.

Figure 2:
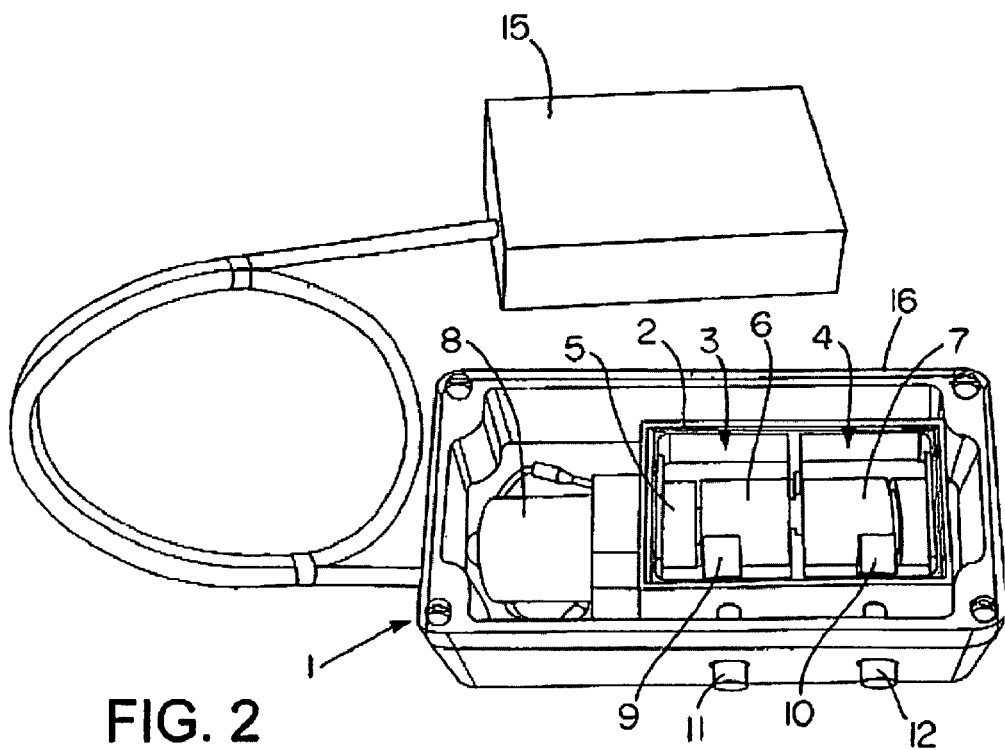
FIG. 2 is a schematic perspective view showing the portable demonstration apparatus of FIG. 1 coupled to a control system including a graphical user interface and control system program and packaged in a portable hand carrying type case.

The additional amount of current drawn or power absorbed by the drive motor or strain induced in the drive shaft, which may vary depending on the friction or power loss characteristics of the different fluids being tested, may be monitored and compared in a computer based acquisition system 15 schematically shown in FIG. 2 to provide an indication of reduced or increased friction between the rotating test shaft 5 and the actuated friction member 9 or 10. This output can be read either on a digital meter or some other data acquisition system which may include a display panel to display the comparison data of the friction or power loss characteristics of the different fluids being compared.

The comparison data may be obtained at a point of presentation or sale, and may be viewed interpersonally, in a small group, organizationally, publicly, or through mass media. Also the comparison data may be obtained through a communications network including the Internet.

The drive motor 8, test shaft 5 and associated piston actuated friction members 9, 10 may be packaged in a portable hand carrying case 16 of suitable type as schematically shown in FIG. 2 along with the control system 15 and its own power supply which may be a battery or fuel cell. Alternatively, an adaptor and plug (not shown) may be provided for plugging the apparatus into an electrical outlet. While the portable apparatus 1 is shown with only two fluid measurement chambers 3, 4, it will be appreciated that more than two such chambers with associated test shaft portions and friction applying members may be provided for comparing the characteristics of more than two fluid samples if desired.

Although only a few embodiments of the present invention have been described, it should be appreciated that many modifications can be made without departing from the spirit and scope of the invention. All such modifications are intended to be included within the scope of the present invention, which is to be limited only by the following claims.

What is claimed is:

1. A method of demonstrating friction or power loss characteristics of different fluids utilizing a portable demonstration apparatus having different fluid chambers for receiving samples of the different fluids, comprising the steps of placing samples of the different fluids in the different chambers, establishing friction or power loss characteristics of the different fluid samples within the different chambers, comparing the friction or power loss characteristics of the different fluid samples, and displaying comparison data of said friction or power loss characteristics of the different fluid samples;

wherein the friction or power loss characteristics of each fluid sample is established by using piston actuated friction shoes applying substantially the same friction or force at different times to different portions of a rotating test shaft while immersed in the different fluid samples and driven by a drive shaft of an electric drive motor at a substantially constant speed, and comparing, for the different fluid samples, an additional amount of current drawn or power absorbed by the drive motor or strain induced in the drive shaft during application of the friction or force to the different portions of said test shaft.

2. The method of claim 1 wherein separate friction shoes are used to apply substantially the same friction or force to the different portions of the test shaft at different times while immersed in the different fluid samples.

3. The method of claim 1 wherein the comparison data is visually displayed.

4. The method of claim 1 wherein the comparison data is obtained at a point of presentation or sale.

5. The method of claim 4 wherein the comparison data is viewed interpersonally, in a small group, organizationally, publicly, and/or through mass media.

6. The method of claim 1 wherein the comparison data is obtained through a communications network.

7. The method of claim 6 wherein the communications network is the Internet.

8. The method of claim 1 wherein the fluids are lubricants or lubricant additives.

9. The method of claim 1 wherein the fluids are engine lubricant treatments for vehicle motor oils.

10. A portable apparatus for demonstrating friction or power loss characteristics of different fluids, comprising different fluid chambers for receiving samples of the different fluids, a test shaft having different portions received in the different fluid chambers for immersion in the different fluid samples, an electric drive motor for rotating the test shaft at a substantially constant speed, piston actuated friction shoes for applying substantially the same amount of friction or force at different times to the different portions of the test shaft while the test shaft is immersed in the different fluid samples and the test shaft is being rotated at a substantially constant speed for establishing a friction or power loss characteristic for each of the fluid samples within the respective chambers, and a control system for comparing and displaying comparative data of the friction or power loss characteristics of the different fluid samples;

wherein the drive motor includes a drive shaft that drives the test shaft, and the control system includes means for comparing, for the different fluid samples, an additional amount of current drawn or power absorbed by the drive motor or strain induced in the drive shaft when substantially the same friction or force is applied at different times to the different portions of said test shaft.

11. The apparatus of claim 10 further comprising means for obtaining the comparison data at a point of presentation or sale.

12. The apparatus of claim 11 wherein the comparison data is viewed interpersonally, in a small group, organizationally, publicly, and/or through mass media.

13. The apparatus of claim 10 wherein the comparison data is obtained through a communications network.

14. The apparatus of claim 13 wherein the communications network is the Internet.

15. The apparatus of claim 10 further comprising a housing containing the fluid chambers, the drive motor and the test shaft.

16. The apparatus of claim 10 which is packaged in a portable hand carrying type case.

* * * * *